United States Patent
Davis

(10) Patent No.: US 8,491,616 B2
(45) Date of Patent: Jul. 23, 2013

(54) SYSTEM AND METHOD FOR CORNEAL ASTIGMATIC AXIS MARKING

(76) Inventor: Andrew Davis, Bellevue, WA (US)

( * ) Notice: Subject to any disclaimer, the term of this patent is extended or adjusted under 35 U.S.C. 154(b) by 404 days.

(21) Appl. No.: 12/417,573

(22) Filed: Apr. 2, 2009

(65) Prior Publication Data

US 2009/0254108 A1    Oct. 8, 2009

Related U.S. Application Data

(60) Provisional application No. 61/072,758, filed on Apr. 2, 2008.

(51) Int. Cl.
*A61F 9/00* (2006.01)

(52) U.S. Cl.
USPC .......................................................... 606/166

(58) Field of Classification Search
USPC ................... 600/249; 606/107, 116, 166, 186
See application file for complete search history.

(56) References Cited

U.S. PATENT DOCUMENTS

| | | | |
|---|---|---|---|
| 3,783,873 A * | 1/1974 | Jacobs ........................... 606/151 |
| 4,417,579 A | 11/1983 | Soloviev et al. |
| 4,476,862 A | 10/1984 | Pao |
| 4,705,035 A | 11/1987 | Givens |
| 4,713,535 A | 12/1987 | Rhoades |
| 4,739,761 A * | 4/1988 | Grandon ........................ 606/166 |
| 5,013,319 A | 5/1991 | Davis |
| 5,104,214 A | 4/1992 | Sims |
| 5,314,439 A | 5/1994 | Sugita |
| 6,045,562 A | 4/2000 | Amano et al. |
| 6,217,596 B1 | 4/2001 | Farah |
| 6,527,788 B1 | 3/2003 | Hellenkamp |
| 6,673,069 B1 * | 1/2004 | Hood ............................... 606/41 |
| 6,776,756 B2 | 8/2004 | Feldon et al. |
| 2002/0082628 A1 | 6/2002 | Hellenkamp |
| 2003/0216763 A1 * | 11/2003 | Patel ............................. 606/166 |
| 2005/0096639 A1 | 5/2005 | Slatkine et al. |
| 2005/0203554 A1 * | 9/2005 | Dykes ........................... 606/166 |
| 2007/0121067 A1 | 5/2007 | Davis |
| 2008/0228210 A1 | 9/2008 | Davis |
| 2009/0287232 A1 | 11/2009 | Davis |

FOREIGN PATENT DOCUMENTS

JP    07231875    9/1995

* cited by examiner

*Primary Examiner* — Ryan Severson
(74) *Attorney, Agent, or Firm* — Lowe Graham Jones PLLC

(57) ABSTRACT

The present invention includes a corneal marker having an adjustable element providing for orientation of the marker to the astigmatic axis of a patient's eye under examination, a handle secured to the corneal marker and a stem secured to and extending below the handle. The stem is weighted to facilitate alignment of the corneal marker to the corneal surface of the patient's eye under examination during corrective eye surgery according to the corneal light reflex from the eye in response to an illumination source.

28 Claims, 7 Drawing Sheets

SYSTEM AND METHOD FOR CORNEAL ASTIGMATIC AXIS MARKING

PRIORITY CLAIM

This application claims priority from earlier filed U.S. Provisional Patent Application Ser. No. 61/072,758 filed Apr. 2, 2008. The foregoing application is hereby incorporated by reference in its entirety as if fully set forth herein.

FIELD OF THE INVENTION

This invention relates generally to an ocular marking system and method and, more specifically, a corneal marking system and method to mark the astigmatic axis on the corneal surface of the eye prior to a surgical procedure to correct the ocular condition of astigmatism.

BACKGROUND OF THE INVENTION

Astigmatism, an optical defect which blurs vision, is usually caused by an irregular curvature of the cornea. In a perfectly shaped eye, the cornea is spherical, and bends all incoming light in the same way, producing a sharply focused image on the back of your eye (retina). In individuals with astigmatism, the cornea is asymmetrically curved, similar to the surface of a football, with one axis of the ball curved more steeply than the opposite axis of the ball. This causes the light rays to be bent differently, which causes the image to be blurred.

The blurred vision from the astigmatism can be measured and is designated as the astigmatic refractive error. The astigmatic refractive error is measured in terms of its power and axis. The astigmatic power is measured in diopters, and the axis is measured in degrees representing the direction on a 360 degree scale. The axis reflects the direction of the steepest or flattest meridian of the cornea. The axis of astigmatism is unique to each individual.

The goal of treating astigmatism is to address the uneven curvature that causes blurred vision. Astigmatism may be corrected with eyeglasses, contact lenses, or surgery. Surgical correction of astigmatism can include laser (such as Lasik or Prk) as well as LRI (Limbal Relaxing Incisions, which are deep incisions in the peripheral cornea that flatten the steep meridian) and astigmatic intraocular lenses (at the time of cataract surgery).

A cataract is a condition where the normally clear lens of the eye becomes progressively opaque. This opacification typically occurs over an extended period of time, and the amount of light that passes through the lens decreases with increasing degrees of opacity. As the ability of the cataract lens to transmit light decreases the ability of the eye to perceive images also decreases. Blindness ultimately can result. Since there are no known methods for eliminating the opacity of a cataract lens, it generally is necessary to surgically remove the opaque lens to permit the unobstructed passage of light through the pupil to the retina.

In cataract surgery, the cloudy natural lens is removed from the eye. The focusing power of the natural lens can be restored by replacing it with a permanent artificial lens or intraocular lens (IOL) implant. These lenses are placed in the eye and thus closely simulate the optics of the natural lens which they are replacing. During cataract surgery, the astigmatic error can be corrected by either performing Limbal Relaxing Incisions in the peripheral cornea to flatten the steeper meridian, or by inserting a specialized IOL which can correct the astigmatism (a toric IOL).

Regardless of whether astigmatism is corrected with an LRI or with a toric intraocular lens, it is essential to align the surgical intervention with the exact astigmatic axis. Prior to the surgery it is necessary to mark the astigmatic axis onto a patient's cornea as accurately as possible.

A variety of methods and instruments are currently used to mark the cornea prior to surgery. Most involve a small hand-held instrument (e.g., U.S. Pat. No. 6,217,596) that is pressed against the cornea prior to surgery, marking reference horizontal or vertical axis. After the eye surgery has started, and the patient is lying down, the reference marks are used to mark the cornea a second time at the direction of the astigmatic axis. This two-step methodology has several shortcomings and introduces several significant sources of error. In particular, error is introduced when the surgeon uses the alignment reference marks made in the first step to then mark the astigmatic axis in the second step. While the alignment is done while the patient is sitting upright, the marking is done while the patient is lying down. The eye undergoes movement within the socket comprising translation and rotation ("cyclotorsion") as the patient is moved from the upright measuring position to the prone surgery position. Multiple techniques known in the art to accommodate this movement include those disclosed in U.S. Pat. No. 4,476,862 and U.S. Pat. No. 4,705,035. If the eye movement is not taken into consideration when the patient lies down the direction of the axis of astigmatism will not be properly accounted for. Mathematically, missing the axis of astigmatism to be treated by 10 to 15 degrees can lead to a treatment under-correction of 50% or more.

Finally, the change in orientation encountered with the patient lying down with surgeon now approaching the patient from the side or from the forehead can be inherently confusing when attempting to mark the axis which was measured with the patient sitting. Difficulty with centration and rotation compound the multiple errors already introduced.

One system and method that avoids many of these problems is described in U.S. patent application Ser. No. 12/047,261, which is directed to a corneal marking device assembly mounted onto a trial frame apparatus that can be adjusted by using the adjustment features on the trial frame apparatus. The corneal marking device assembly provides the stabilized structure through which the surgeon can observe the eye, measure characteristic features of the eye and mark the corneal surface with a corneal marking device housed in the corneal marking device assembly. While this system reduces disadvantages associated with traditional hand-held devices, however, the use of a trial frame apparatus can be cumbersome.

Accordingly, there is a need for a non-cumbersome system and method that reduces errors associated with the traditional two-step methodology for marking the astigmatic axis on the cornea.

SUMMARY OF THE INVENTION

The present invention addresses the systematic errors introduced by marking the cornea using traditional hand-held device in a two-step methodology by providing a novel system and method for marking the astigmatic axis in one simple step while a patient is sitting prior to eye surgery.

A preferred embodiment of the present invention includes a corneal marker, a handle secured to the corneal marker and a stem secured to and extending below the handle. The stem is weighted to facilitate alignment of the corneal marker to the corneal surface of a patient's eye under examination during corrective eye surgery according to the corneal light reflex from the eye in response to an illumination source. With the preferred corneal marking device, the corneal marker has a substantially cylindrical central hub and a plurality of radial blades connected and substantially perpendicular to the central hub. A substantially cylindrical ring gauge is configured to rotatably fit adjacent the central hub. Preferably the handle includes a first substantially horizontal portion secured to the stem and a second substantially vertical portion secured to at least one of the corneal marker and ring gauge.

In one embodiment, the plurality of radial blades are configured to leave a perceptible impression upon the corneal surface of the eye under examination. In an alternative embodiment, the plurality of radial blades are configured to apply ink to the corneal surface of the eye under examination.

In an alternative embodiment, the corneal marking device includes a rotation member configured to allow movement of at least one of the corneal marker and ring gauge independent of the handle to facilitate alignment of the plurality of radial blades to the corneal surface of a patient's eye under examination during corrective eye surgery.

A method for marking a corneal surface of an eye of a patient includes adjusting a corneal marking device to the desired setting based on a patient's eye under examination; illuminating the eye under examination with a light source; retracting eyelid of eye under examination; observing the corneal light reflex produced by the light source; aligning a corneal marking device associated with the mounting apparatus with an unobstructed corneal surface of the eye under examination using a weight secured to the corneal marking device to position the corneal marking device based on the corneal light reflex produced by the light source; and if the corneal marking device is aligned, marking the unobstructed corneal surface of the eye under examination. The patient's eye not under examination may be covered.

As will be readily appreciated from the foregoing summary, the present invention provides an improved corneal marking system and method to mark the corneal surface of the eye prior to a surgical procedure to correct the ocular condition of astigmatism and thus improve the outcome of astigmatic refractive surgeries.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

Figure 1:
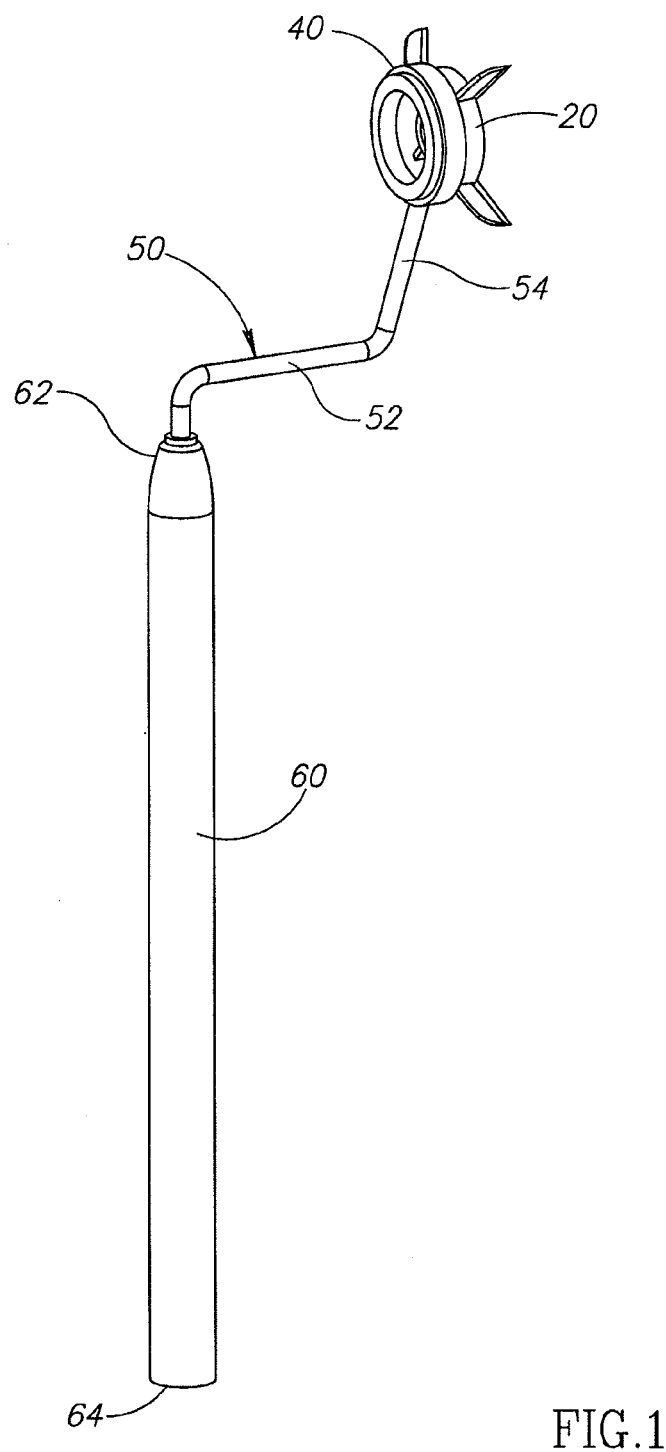
FIG. 1 is an isometric view of the preferred embodiment corneal marker of the present invention.

A description of the preferred embodiments of the present invention is presented with reference to FIGS. 1-9. FIG. 1 shows one embodiment of a corneal marking device 10 of the present invention. The corneal marking device 10 includes a corneal marker 20, a ring gauge 40, a handle 50 and a weighted stem 60. The preferred weighted stem 60 includes a proximate end 62 located near the handle 50 and a distal end 62 located remote to the handle 50. The stem 60 may be of varying lengths or thickness, but is preferably of sufficient weight to facilitate orientation of the handle 50 to a patient's eye under examination when in operation, but not so heavy to be uncomfortable for the surgeon during operation of the corneal marking device 10.

The handle 50 is preferably sized to fit comfortably within a surgeon's hand, but may be of varying lengths or thickness. The handle 50 is attached to the proximate end 62 of the stem 60 and extends away from the stem to support the corneal marker 20 and ring gauge 40. The handle 50 preferably includes a generally horizontal handle portion 52 proximate to the point of connection with the stem 60 and a generally vertical handle portion 54 that connects to and supports the corneal marker 20 and ring gauge 40. In a preferred embodiment, the horizontal handle portion 52 attaches to the stem 60 at a 90 degree angle and is relatively short in length. In a preferred embodiment, the horizontal handle portion 52 joins the vertical handle portion 54 at an angle of approximately 135 degrees, and the vertical handle portion 54 in turn joins the ring gauge 40 at an angle of approximately 135 degrees, resulting in stem 60 and ring gauge 40 being generally parallel to each other. The shapes, lengths, and angles of association as between the stem 60, the handle 50 and the corneal marker 20 and ring gauge 40 supported thereby may vary greatly within the scope of the present invention.

Figure 2:
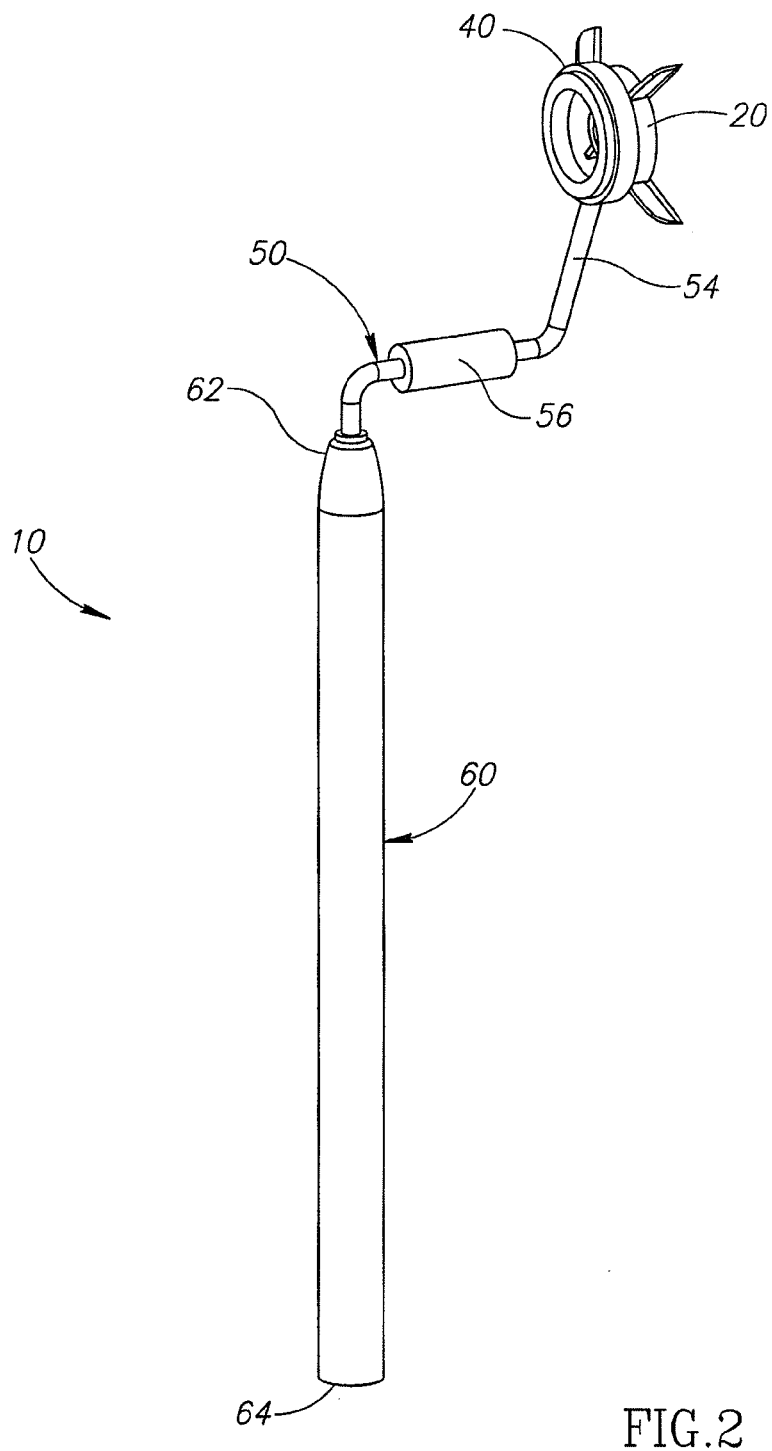
FIG. 2 is an isometric view of one embodiment of the present invention showing the corneal marker, ring gauge, and handle and stem assembly, wherein the handle and stem assembly further includes a rotation feature that allows the stem to rotate freely with respect to the handle.

FIG. 2 shows an alternative embodiment of the corneal marking device 10 wherein a part of the horizontal handle portion 52 is substantially encased by a cylindrical attachment 56 that is configured to allow the horizontal handle portion 52 to rotate freely within the cylindrical attachment 56, making it easier for the surgeon to hold the handle without interfering with the freedom to rotate and otherwise maintain the corneal marking device in the desired position.

A preferable aspect of the present invention is that the stem 60 acts as a weight or anchor to orient the corneal marker or means for marking the astigmatic axis of an unobstructed corneal surface of an eye under examination according to the corneal light reflex from the eye in response to an illumination source while the surgeon is holding the handle 50. In the preferred embodiment, the corneal marker or means for marking includes the corneal marker 20 and ring gauge 40, but other known marking devices may also be used. The use of a weighted stem in the present invention acts to offset and therefore force into a generally vertical position the corneal marker 20 and ring gauge 40 to allow the surgeon to align the corneal marking device 10 to enable proper marking of the astigmatic axis in a single-step process. In addition to the preferred embodiment described above, various other embodiments of the handle 50 and stem 60 assemblies are contemplated to facilitate this aspect of the present invention. For example, in one embodiment, the horizontal handle portion 52 and the vertical handle portion 54 may be separate but movably connected via an attachment that allows the horizontal handle portion 52 and the vertical handle portion 54 to move independent of each other, again to facilitate maintenance of the corneal marking device in the desired position. In yet another embodiment, the corneal marking device 10 may include a stem 60 connected only to a vertical handle portion 54. In yet another embodiment, the stem 60 may be configured as a small geometric weight to facilitate orientation of the vertical handle portion 54 vertically and parallel the patient's head.

Figure 3:
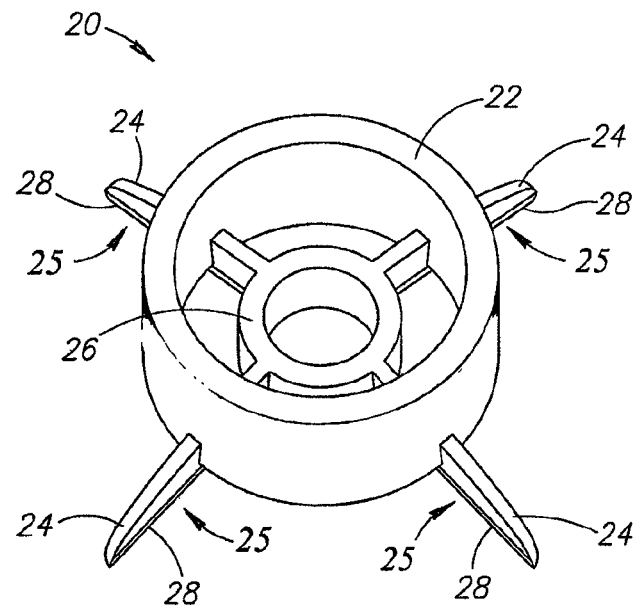
FIG. 3 is an isometric view of the preferred embodiment of the corneal marker of the present invention.

FIG. 3 shows in greater detail the preferred corneal marker 20 of the corneal marking device 10 that is used to mark the patient's eye under examination. The corneal marker 20 preferably includes a substantially cylindrical central hub 22 that is attached to four perpendicular radial blades 24 that flare outward from the central hub 22 and are joined at a central ring 26 located within the diameter of the central hub 22. The central ring 26 is the preferred alignment assembly used to align the corneal marking device 10 according to the corneal light reflex of the patient's eye under examination. In alternative embodiments, alignment assemblies of different shapes and structures may be used, for example, an oval, square, rectangle or other shaped structure, preferably located within the diameter of the central hub 22, so long as it facilitates alignment of the corneal marking device 10 according to the corneal light reflex of the patient's eye under examination through use of some type of cross-hair configuration. Each of the four blades 24 is preferably curved along a first side 25 to match the corneal curvature of an eye. Each of the four blades is preferably configured with a sharp edge 28 along the first side 25 to enable marking, but not cutting, of the cornea. Marking may be accomplished solely by the pressure or the sharp edge 28 of the blades 24 upon the cornea, which leaves a perceptible impression for a period of time, or by application of ink to the sharp edge 28 of the blades 24, which in turn leaves visible marking on the cornea. As shown further with reference to FIG. 4, an alternative embodiment of the corneal marker 20 may include threads 32 along the outside surface 30 of the central hub 22.

Figure 5:
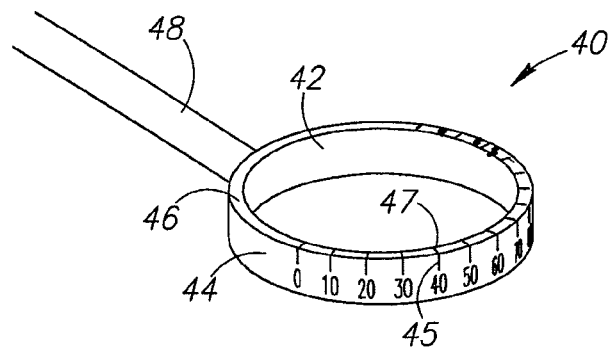
FIG. 5 is an isometric view of the preferred embodiment of the corneal marker ring gauge of the present invention.

The ring gauge 40 of the corneal marking device 10 is better understood with reference to FIG. 5. In a preferred embodiment, the ring gauge 40 is substantially cylindrical in shape, and includes an inner surface 42, an outer surface 44, a top surface 46 and a means of connection 48 to the vertical handle portion 54. The diameter of the ring gauge 40 is such that the inner surface 42 of the ring gauge 40 fits securely adjacent the outside surface 30 of the central hub 20 around the outer diameter of the central hub 20. The ring gauge 40 preferably includes markings 45 on the outer surface 44 and markings 47 on the top surface 46 corresponding to 0-180 degrees in 10 degree increments. In alternative embodiments, the markings may be located on additional, fewer than or other surfaces of the ring gauge 40. The means of connection 48 between the ring gauge 40 and the vertical handle portion 54 of the handle 50 may include molding the ring gauge 40 directly to the handle 50, or otherwise permanently connecting the ring gauge 40 and the handle 50, or may include a detachable means of connection between the ring gauge 40 and the handle 50 (not show), such as but not limited to mechanical fittings, clasps, or other connections well known in the art.

Figure 4:
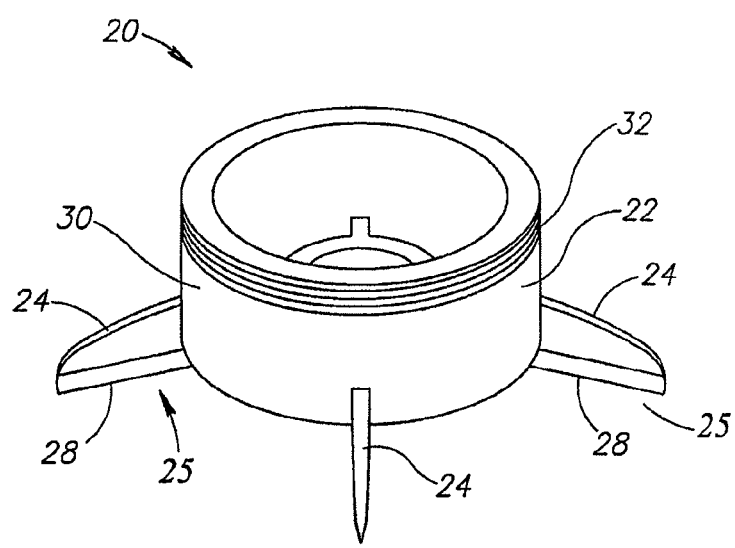
FIG. 4 is an isometric view of the one embodiment of the corneal marker of the present invention showing optional corneal marker cap threads.
Figure 6:
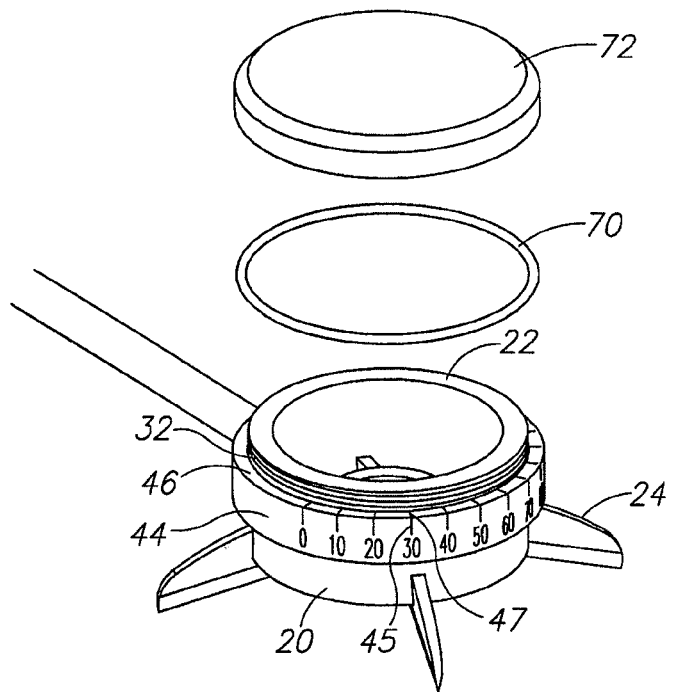
FIG. 6 is a partial exploded isometric view of one embodiment of the present invention showing the corneal marker and ring gauge along with optional washer and cap.
Figure 7:
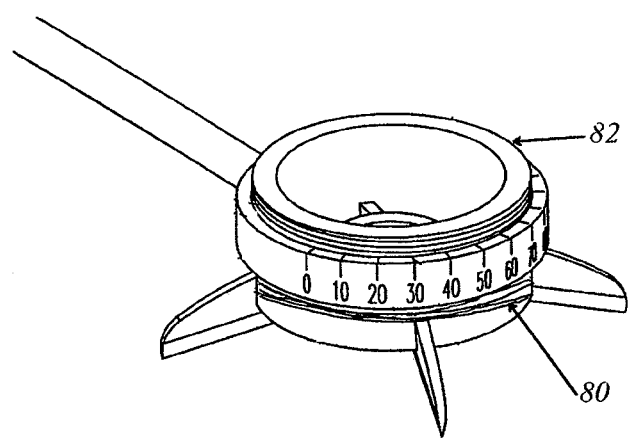
FIG. 7 is an isometric view of one embodiment of the present invention incorporating a cylindrical compression spring.

FIG. 6 shows a preferred embodiment of the corneal marking device 10 shown in FIG. 4, wherein the threads 32 are used in conjunction with a washer 70 and cap 72 having internal threads (not shown) corresponding to the threads 32 to enable the cap to be removably attached to the central hub 22. When used with the washer 70, this secures the ring gauge 40 to the central hub 22 while allowing the user to manually rotate the central hub 22 inside the ring gauge 40 without excessive force to align at least one of the radial blades 24 with the markings 45 on the outer surface 44 of the ring gauge 40 for designation of the astigmatic axis. In contemplated alternative embodiments, various other means may be used to maintain the ring gauge 40 adjacent to the central hub 22 while allowing the user to manually rotate the central hub 22 inside the ring gauge 40 without excessive force, e.g., using friction fit, a snap ridge movably connecting the ring gauge 40 to the central hub 22, etc. In an alternative embodiment, shown in FIG. 7, a cylindrical compression spring 80 may be oriented around the central hub 22 positioned between the radial blades 24 and ring gauge 40 to allow the manual rotation of the radial blades around the central hub. In this embodiment, the central hub 22 may further include a protruding lip 82 positioned to maintain the ring gauge 40 adjacent to the central hub 22 while allowing the user to manually rotate the central hub 22 inside the ring gauge 40 without excessive force. This embodiment would further allow a means of limiting the force transmitted to the cornea by the radial blades 24 in operation of the corneal marking device 10.

Figure 8:
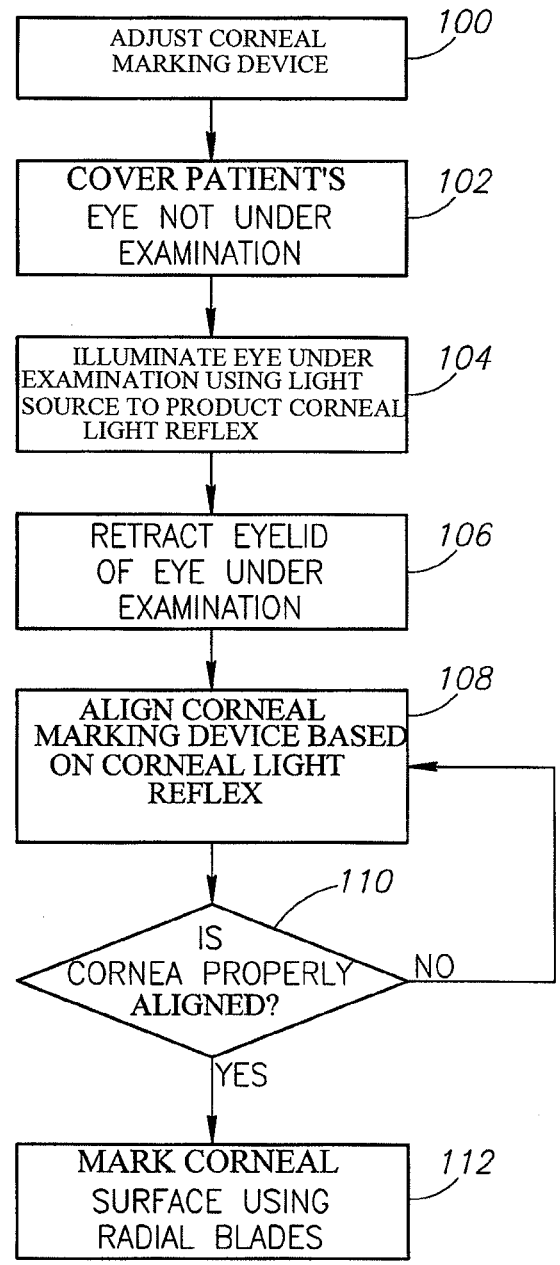
FIG. 8 is flow diagram showing a preferred method of corneal marking by a surgeon utilizing a preferred embodiment of the present invention.
Figure 9:
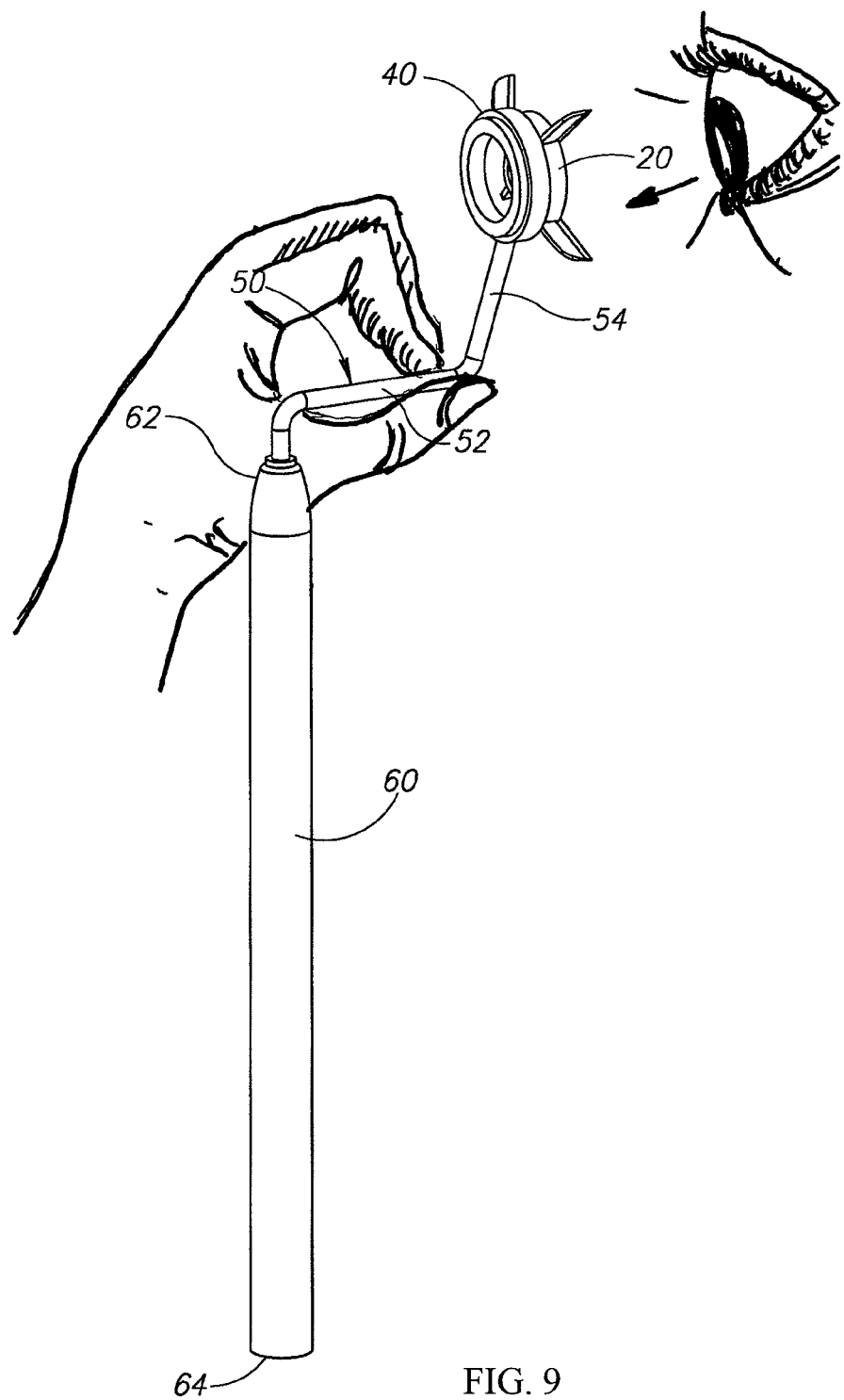
FIG. 9 is an isometric view of one embodiment of the corneal marking device of the present invention showing preferred hand placement for utilization of the device.

The preferred method of corneal marking by a surgeon is described with reference to the flow diagram of FIG. 8 utilizing the assembled corneal marking device 10 shown more fully in FIGS. 1 and 6, and in operational context as provided by reference to FIG. 9. At block 100, the corneal marker 20 is dialed or oriented so that one of the four blades 24 is aligned to the desired axis on the ring gauge 40 using the markings 45 on the outer surface 44 or the markings 47 on the top surface 46 of the ring gauge 40 for designation of the astigmatic axis of the patient's eye under examination. At block 102, in a preferred embodiment, a patient's eye not under examination is covered.

At block 104, the patient eye under examination is illuminated to allow the surgeon to observe the resultant corneal light reflex. This preferably occurs after anesthetic drops are applied to the patient's eye under examination and the patient is in a sitting position. In the preferred embodiment, the eye is illuminated using a fixation light held by the surgeon in one hand while holding the corneal marking device 10 in the other hand. This may also be accomplished using other sources of illumination held by the surgeon, other persons or associated with a movable or stationary fixture.

At block 106, the eyelid of the patient's eye under examination is retracted. At block 108, the corneal marking device 10 is aligned such that the corneal light reflex is aligned in the central ring 26 located within the diameter of the central hub 22. This is preferably accomplished by using the sight line of the fixation light (similar to aiming a rifle) to observe the resultant corneal light reflex. The corneal marking device is preferably held with the surgeon's thumb underneath the horizontal handle portion 52 of the handle 50 with the surgeon's index or middle finger on top of the horizontal handle portion 52, but may be held in a variety of ways according to surgeon preference. The handle 50 is preferably held tightly enough to position the corneal marking device 10 while still allowing the weight of the stem 60 to maintain the vertical handle portion 54 in a vertical position.

A check is made at decision block 110 whether the cornea is properly aligned based on the corneal light reflex being aligned in the central ring 26 located within the diameter of the central hub 22. If not, the logic returns to block 108. If the cornea is properly aligned, the logic continues to block 112, where the four blades 24 of the corneal marking device 10 are applied to the cornea of the patient's eye under examination with sufficient force to leave four radial marks on the corneal surface from the sharp edge 28 along the first side 26 of the blades 24. Marking may be accomplished solely by the pressure or the sharp edge 28 of the blades 24 of the corneal marking device 10 upon the cornea, which leaves a perceptible impression for a period of time, or by application of ink to the sharp edge 28 of the blades 24, which in turn leaves visible marking on the cornea.

While the preferred embodiment of the invention has been illustrated and described, as noted above, many changes can be made without departing from the spirit and scope of the invention. For example, the interface between the corneal marker and ring gauge may be altered such that the ring gauge sits within the inner diameter of the corneal marker to provide rotational alignment of the radial blades. In yet an alternative embodiment, the radial blades may be internal to a larger corneal marker rather than flare outward from the corneal marker. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A corneal marking device, comprising;
a corneal marker;
a handle secured to the corneal marker; and
a weighted stem secured to the handle,
wherein the corneal marking device is configured such that the weighted stem acts as a counterweight to the corneal marker to stabilize the corneal marking device in a vertical orientation with the stem below the corneal marker to align the corneal marker to the corneal surface of a patient's eye under examination during corrective eye surgery according to the corneal light reflex from the eye in response to an illumination source.

2. The corneal marking device of claim 1, wherein the corneal marker comprises a plurality of radial blades.

3. The corneal marking system of claim 2, wherein the plurality of radial blades are configured to leave a perceptible impression upon the corneal surface of the eye under examination.

4. The corneal marking system of claim 2, wherein the plurality of radial blades are configured to apply ink to the corneal surface of the eye under examination.

5. The corneal marking device of claim 1, further comprising a rotation member configured to allow movement of the corneal marker independent of the handle to facilitate alignment of the plurality of radial blades to the corneal surface of a patient's eye under examination during corrective eye surgery.

6. The corneal marking device of claim 1, wherein
the stem has a longitudinal axis;
the handle comprises at least one portion having a longitudinal axis secured to the stem; and
the angle between the longitudinal axis of the stem and the longitudinal axis of the at least one portion of the handle is greater than ten degrees.

7. The corneal marking device of claim 1, wherein the handle further comprises a rotation member configured to allow movement of the corneal marker in response to the downward force of the weighted stem to stabilize the corneal marking device in a vertical orientation with the weighted stem below the corneal marker.

8. A corneal marking device, comprising;
a corneal marker having a substantially cylindrical central hub;
a plurality of radial blades connected to the central hub, the plurality of radial blades defining a corneal marker plane;
a substantially cylindrical ring gauge configured to rotatably fit adjacent the central hub;
a handle secured to the at least one of the corneal marker and ring gauge; and
a stem secured to the handle, the stem configured to act as a counterweight to the corneal marker to facilitate alignment of the plurality of radial blades to the corneal surface of a patient's eye under examination during corrective eye surgery, the weighted stem having a longitudinal axis, wherein the longitudinal axis of the weighted stem is substantially parallel to the corneal marker plane.

9. The corneal marking device of claim 8, wherein the corneal marker further comprises an alignment assembly for aligning the corneal marking device.

10. The corneal marking device of claim 9, wherein the alignment assembly comprises a central ring.

11. The corneal marking device of claim 8, wherein the ring gauge rotatably fits adjacent the outside surface of the central hub.

12. The corneal marking device of claim 8, wherein the ring gauge includes degree markings configured to orient the radial blades in the direction of the astigmatic axis of the patient's eye under examination.

13. The corneal marking device of claim 12, wherein the degree markings range from 0-180 degrees.

14. The corneal marking device of claim 8, wherein the plurality of radial blades are configured to leave a perceptible impression upon the corneal surface of the eye under examination.

15. The corneal marking device of claim 8, wherein the plurality of radial blades are configured to apply ink to the corneal surface of the eye under examination.

16. The corneal marking device of claim 8, further comprising a rotation member configured to allow movement of at least one of the corneal marker and ring gauge independent of the handle to facilitate alignment of the plurality of radial blades to the corneal surface of a patient's eye under examination during corrective eye surgery.

17. The corneal marking device of claim 8, wherein
at least one portion of the handle has a longitudinal axis; and
the angle between the longitudinal axis of the stem and the at least one portion of the handle at the point where the stem is secured to the handle is approximately between 45 degrees and 135 degrees.

18. The corneal marking device of claim 8, wherein the handle further comprises a rotation member configured to allow movement of the corneal marker in response to the downward force of the weighted stem to stabilize the corneal marking device in a vertical orientation with the weighted stem below the corneal marker.

19. A corneal marking system for corrective eye surgery, comprising:
a means for illuminating a patient's eye under examination to observe the corneal light reflex produced by the illuminating means;
a means for marking the eye; and
a means for aligning the corneal marking device with an unobstructed corneal surface according to the corneal light reflex, wherein the means for aligning the corneal marking device comprises a stem configured to act as a counterweight to the corneal marker and having a longitudinal axis; and a handle having at least one portion with a longitudinal axis secured to the stem, wherein the angle between the longitudinal axis of the stem and the longitudinal axis of the at least one portion of the handle at the point where the stem is secured to the handle is approximately between 45 degrees and 135 degrees.

20. The corneal marking system of claim 19, wherein the means for illuminating a patient's eye under examination is a fixation light.

21. The corneal marking system of claim 19, wherein the means for aligning the corneal marking device further comprises a central ring.

22. The corneal marking system of claim 19, wherein the means for marking the eye under examination comprises a plurality of radial blades.

23. The corneal marking system of claim 22, wherein the plurality of radial blades are configured to leave a perceptible impression upon the corneal surface of the eye under examination.

24. The corneal marking system of claim 22, wherein the plurality of radial blades are configured to apply ink to the corneal surface of the eye under examination.

25. A method for marking a corneal surface of an eye of a patient, comprising:

adjusting a corneal marking device to the desired setting based on a patient's eye under examination, wherein the corneal marking device comprises a corneal marker, a handle secured to the corneal marker, and a weighted stem configured to act as a counterweight to the corneal marker secured to the handle;

illuminating the eye under examination with a light source;

retracting eyelid of eye under examination;

with the patient in a sitting position, stabilizing the corneal marking device in a vertical orientation using the stem to force the corneal marker into the stabilized vertical orientation with the stem below the corneal marker;

observing the corneal light reflex produced by the light source;

aligning the corneal marker with an unobstructed corneal surface of the eye under examination to position the corneal marker device based on the corneal light reflex produced by the light source; and if the corneal marking device is aligned, marking the unobstructed corneal surface of the eye under examination.

26. The method of claim 25, further comprising covering the patient's eye not under examination.

27. The method of claim 25, wherein marking the unobstructed corneal surface of the eye under examination includes making a perceptible impression upon the corneal surface of the eye.

28. The method of claim 25, wherein marking the unobstructed corneal surface of the eye under examination includes applying ink to the corneal surface of the eye.

* * * * *